(12) United States Patent
Lai et al.

(10) Patent No.: US 7,399,795 B2
(45) Date of Patent: Jul. 15, 2008

(54) SURFACE MODIFICATION OF CONTACT LENSES

(75) Inventors: Yu-Chin Lai, Pittsford, NY (US);
Edmond T. Quinn, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 192 days.

(21) Appl. No.: 11/442,826

(22) Filed: May 30, 2006

(65) Prior Publication Data

US 2006/0217454 A1    Sep. 28, 2006

Related U.S. Application Data

(63) Continuation of application No. 10/728,531, filed on Dec. 5, 2003, now Pat. No. 7,084,188.

(51) Int. Cl.
*C08F 290/96*  (2006.01)
*G02C 7/04*  (2006.01)

(52) U.S. Cl. ............... 523/107; 523/106; 424/422; 351/160 H

(58) Field of Classification Search ............... 523/107; 351/160 H
See application file for complete search history.

(56) References Cited

U.S. PATENT DOCUMENTS

| | | | |
|---|---|---|---|
| 3,408,429 A | 10/1968 | Wichterle | |
| 3,496,524 A | 2/1970 | Stavis et al. | |
| 3,759,968 A | 9/1973 | Berger et al. | |
| 4,084,459 A | 4/1978 | Clark | |
| 4,136,250 A | 1/1979 | Mueller et al. | |
| 4,153,641 A | 5/1979 | Deichert et al. | |
| 4,192,827 A | 3/1980 | Mueller et al. | |
| 4,197,266 A | 4/1980 | Clark et al. | |
| 4,486,577 A | 12/1984 | Mueller et al. | |
| 4,605,712 A | 8/1986 | Mueller et al. | |
| 4,717,498 A | 1/1988 | Maxon | |
| 4,740,533 A | 4/1988 | Su et al. | |
| 4,868,260 A | 9/1989 | Kawaguchi | |
| 4,910,277 A | 3/1990 | Bambury et al. | |
| 4,933,406 A | 6/1990 | Anan et al. | |
| 4,954,587 A | 9/1990 | Mueller | |
| 4,962,178 A | 10/1990 | Harisiades | |
| 5,034,461 A | 7/1991 | Lai et al. | |
| 5,070,215 A | 12/1991 | Bambury et al. | |
| 5,142,009 A | 8/1992 | Kawaguchi | |
| 5,180,843 A | 1/1993 | O'Lenick, Jr. | |
| 5,206,298 A | 4/1993 | Kawaguchi | |
| 5,250,583 A | 10/1993 | Kawaguchi et al. | |
| 5,260,000 A | 11/1993 | Nandu et al. | |
| 5,271,875 A | 12/1993 | Appleton et al. | |
| 5,296,625 A | 3/1994 | O'Lenick, Jr. | |
| 5,310,779 A | 5/1994 | Lai | |
| 5,344,701 A | 9/1994 | Gagnon et al. | |
| 5,346,946 A | 9/1994 | Yokoyama et al. | |
| 5,358,995 A | 10/1994 | Lai et al. | |
| 5,374,662 A | 12/1994 | Lai et al. | |
| 5,391,591 A | 2/1995 | Kawaguchi et al. | |
| 5,420,324 A | 5/1995 | Lai et al. | |
| 5,496,871 A | 3/1996 | Lai et al. | |
| 5,514,730 A | 5/1996 | Mazurek et al. | |
| 5,661,194 A | 8/1997 | Ando et al. | |
| 5,786,434 A | 7/1998 | Ando et al. | |
| 5,883,152 A | 3/1999 | Anan et al. | |
| 5,929,268 A | 7/1999 | O'Lenick, Jr. | |
| 6,004,542 A | 12/1999 | O'Lenick, Jr. | |
| 6,087,415 A * | 7/2000 | Vanderlaan et al. | 523/105 |
| 6,440,571 B1 * | 8/2002 | Valint et al. | 428/447 |
| 6,599,559 B1 | 7/2003 | McGee et al. | |
| 2002/0082312 A1 | 6/2002 | Lai | |
| 2002/0102415 A1 | 8/2002 | Valint, Jr. et al. | |

FOREIGN PATENT DOCUMENTS

WO    WO01/74932    10/2001

OTHER PUBLICATIONS

Yu-Chin Lai, Richard Ozark, Edmond T. Quinn—Journal of Polymer Science: Part A: Polymer Chemistry, vol. 33, pp. 1773-1782 (1995)—Synthesis and Characterization of $\alpha,\omega$-bis(4-hydroxybutyl) Polydimethylsiloxanes.

ROC (Taiwan) Search Report mailed on Feb. 15, 2007.

* cited by examiner

*Primary Examiner*—Tae H Yoon
(74) *Attorney, Agent, or Firm*—Glenn D. Smith

(57) ABSTRACT

Provided are surface modified contact lenses formed from one or more fumaric- or itaconic-containing prepolymers having reactive functionality that is complimentary to reactive hydrophilic polymers.

6 Claims, No Drawings

SURFACE MODIFICATION OF CONTACT LENSES

CROSS REFERENCE

This application is a continuation of U.S. application Ser. No. 10/728,531, filed on Dec. 5, 2003, now U.S. Pat. No. 7,084,188 herein incorporated by reference.

FIELD OF THE INVENTION

The present invention relates generally to reactive fumaric- and itaconic-containing prepolymers and compositions comprising the prepolymers used in the manufacture of medical devices. More specifically, the present invention relates to surface modified contact lenses formed from one or more functionalized fumaric- or itaconic-containing prepolymers having reactive functionality that is complimentary to reactive, hydrophilic polymers.

BACKGROUND OF THE INVENTION

Medical devices such as ophthalmic lenses made from silicone-containing materials have been investigated for a number of years. Such materials can generally be sub-divided into two major classes, namely hydrogels and non-hydrogels. Non-hydrogels do not absorb appreciable amounts of water, whereas hydrogels can absorb and retain water in an equilibrium state. Hydrogels generally have water content between about 15 to about 80 weight percent. Regardless of their water content, both non-hydrogel and hydrogel silicone medical devices tend to have relatively hydrophobic, non-wettable surfaces that have a high affinity for lipids. This problem is of particular concern with contact lenses.

Fumarate- and fumaramide-containing monomers and compositions comprising the monomers have been developed to make highly oxygen permeable hydrogels which may be used to make biomedical devices including contact lenses. Examples of these fumarate- and fumaramide-containing monomers and compositions can be found in U.S. Pat. No.'s 5,374,662, 5,420,324, and 5,496,871, the contents of each being incorporated by reference herein. Because of the polar character of amide functionality, this class of monomer shows good compatibility with both hydrophobic monomers such as tris(trimethylsiloxy)silane (TRIS) and hydrophilic monomers such as N,N-dimethylacrylamide (DMA). These prior art prepolymers give silicone hydrogels with excellent oxygen permeability and mechanical properties. However, like other silicone hydrogels, they are not wettable enough to be useful as continuous wear lenses unless the surface is treated.

Surface structure and composition determine many of the physical properties and ultimate uses of solid materials. Characteristics such as wetting, friction, and adhesion or lubricity are largely influenced by surface characteristics. The alteration of surface characteristics is of special significance in biotechnical applications where biocompatibility is of particular concern. Therefore, those skilled in the art have long recognized the need for rendering the surface of contact lenses and other medical devices hydrophilic or more hydrophilic. Increasing the hydrophilicity of the contact-lens surface improves the wettability of the contact lenses with tear fluid in the eye. This in turn improves the wear comfort of the contact lenses. In the case of continuous-wear lenses, the surface is especially important. The surface of a continuous-wear lens must be designed not only for comfort, but to avoid adverse reactions such as corneal edema, inflammation, or lymphocyte infiltration. Improved methods have accordingly been sought for modifying the surfaces of contact lenses, particularly high-Dk (highly oxygen permeable) lenses designed for continuous (overnight) wear.

Various patents disclose the attachment of hydrophilic or otherwise biocompatible polymeric chains to the surface of a contact lens in order to render the lens more biocompatible. For example, U.S. Pat. Pub. No. U.S. 2002/0102415 A1 teaches plasma treatment of a fumarate- or fumaramide-containing substrate followed by reaction with other polymers, such as DMA/VDMO copolymer.

Although manufacturing steps such as plasma treatment provide lenses having suitable coatings, it would be desirable to produce a surface treated lens without the need for plasma treatment or corona discharge treatment.

It would be further desirable to provide an improved silicone hydrogel contact lens with an optically clear, hydrophilic surface film that will not only exhibit improved wettability, but which will generally allow the use of a silicone hydrogel contact lens in the human eye for an extended period of time. In the case of a silicone hydrogel lens for extended wear, it would be desirable to provide a contact lens with a surface that is also highly permeable to oxygen and water. Such a surface treated lens would be comfortable to wear in actual use and would allow for the extended wear of the lens without irritation or other adverse effects to the cornea.

SUMMARY OF THE INVENTION

In accordance with the present invention, reactive functionalized fumaric- and itaconic-containing prepolymers are disclosed for use with both silicone and non-silicone containing polymeric systems used for biomedical devices, especially contact lenses. The prepolymers have the following schematic representations:

and

wherein $R_1$ is an alkylene that may have ether linkages, $R_2$ and $R_3$ are independently alkyl or phenyl groups, unsubstituted or substituted with halogen and ether linkages, W is O or NH, n is an integer between 1 and 10, m is an integer between 2 and 200, and Y is a residue having a reactive functional group selected from the group consisting of hydroxyl, carboxyl, oxazolone, epoxy and anhydride functional groups. The reactive functional group has complementary reactivity to reactive hydrophilic coating polymers.

The invention is further directed toward medical devices formed of a polymerizable mix comprising the reactive functionalized fumaric- and itaconic-containing prepolymers. Such devices are useful in forming surface modified medical devices without use of treatments such as plasma treatment or corona discharge treatment.

This invention is further directed toward surface treatment of a device containing the prepolymers disclosed herein, for example, silicone contact lenses and other silicone medical devices, including a method of modifying the surface of a contact lens to increase its hydrophilicity or wettability. The surface treatment comprises the attachment of hydrophilic reactive polymer chains to the surface of the contact lens substrate by means of reactive functionalities of the reactive functionalized fumaric- or itaconic-containing prepolymer component in the lens substrate material reacting with complementary reactive functionalities in monomeric units along a hydrophilic reactive polymer. Such surface modification of a contact lens provides a lens having improved compatibility with the eye.

The present invention is also directed to a surface modified medical device, examples of which include contact lenses, intraocular lenses, catheters, implants, and the like, comprising a surface made by such a method.

DETAILED DESCRIPTION OF THE INVENTION

As stated above, the present invention is directed toward reactive fumaric- and itaconic-containing prepolymers for use with copolymerizable polymeric systems used for biomedical devices, especially contact lenses. As used herein, fumaric refers to a derivative of fumaric acid and can be a fumarate (an ester), a fumaramide (an amide) or a residue having both ester and amide functionalities. The fumaric group is a residue of trans-1,2-ethylenedicarboxylate. Therefore, it will be understood that the diastereoisomer of fumarate, maleate, is also intended to be included in the fumaric-containing prepolymers of the present invention. Itaconic refers to derivatives of itaconic acid and has a similar meaning as that of fumaric. In further embodiments of the present invention, the prepolymers are used to make biomedical devices and are useful in contact lens formulations which may be either "soft" or "hard" and which may preferably be hydrogels.

In further embodiments of the present invention, medical devices made with the prepolymers are coated with hydrophilic reactive polymer with complimentary reactive functionalities to the reactive functionalized fumaric- and itaconic-containing medical devices.

The reactive functionalized fumaric- and itaconic-containing prepolymers of the present invention have at least one fumaric or itaconic group. Monomer mixes comprising the prepolymers of the present invention may comprise both thermal- and photoinitiators for curing purposes. The monomer mixes may further comprise at least one additional hydrophilic monomer. Further, the monomer mix may additionally comprise at least one silicone-containing monomer.

As is known in the field, certain crosslinked polymeric materials may be polymerized to form a hard, water-free, xerogel. Xerogels are understood to be unhydrated hydrogel formulations. It was found that such xerogels could be physically altered to, for example, impart optical properties through machining, and then be hydrated and retain their water content.

When the term "polymerization" is used herein we refer to the polymerization of the double bonds of the monomers and prepolymers endcapped with polymerizable unsaturated groups which results in a crosslinked three-dimensional network.

Further, notations such as "(meth)acrylate" or "(meth) acrylamide" are used herein to denote optional methyl substitution. Thus, for example, (meth)acrylate includes both acrylate and methacrylate and N-alkyl-(meth)acrylamide includes both N-alkyl acrylamide and N-alkyl methacrylamide.

The term "prepolymer" denotes a high molecular weight monomer containing polymerizable groups. The monomers added to the monomeric mixture of the present invention may therefore be low molecular weight monomers or prepolymers. Thus, it is understood that a term such as "silicone-containing monomers" includes "silicone-containing prepolymers".

The terms "shaped articles for use in biomedical applications" or "biomedical devices or materials" or "biocompatible materials" mean the hydrogel materials disclosed herein have physicochemical properties rendering them suitable for prolonged contact with living tissue, blood and the mucous membranes.

While the present invention contemplates the use of reactive functionalized fumaric- and itaconic-containing prepolymers for medical devices including both "hard" and "soft" contact lenses, the formulations containing the reactive functionalized fumaric- and itaconic-containing prepolymers of the present invention are thought to be especially useful as soft hydrogel contact lenses. As is understood in the field, a lens is considered to be "soft" if it can be folded back upon itself without breaking.

A hydrogel is a hydrated cross-linked polymeric system that contains water in an equilibrium state. Silicone hydrogels (i.e., hydrogels containing silicone) are usually prepared by polymerizing a mixture containing at least one silicone-containing monomer and at least one hydrophilic monomer. By the term silicone, it is meant that the material is an organic polymer comprising at least five percent by weight silicone (—OSi-linkages), preferably 10 to 100 percent by weight silicone, more preferably 30 to 90 percent by weight silicone. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

The reactive functionalized fumaric- and itaconic-containing prepolymers of the present invention have at least one fumaric or itaconic group. Monomer mixes comprising the prepolymers of the present invention may comprise both thermal- and photoinitiators for curing purposes. The monomer mixes may further comprise at least one additional hydrophilic monomer. Further, the monomer mix may additionally comprise at least one silicone-containing monomer.

The fumaric- and itaconic-containing prepolymers of the present invention are prepared according to syntheses well known in the art and according to the examples disclosed herein. The functionalized fumaric- and itaconic-containing prepolymers of the present invention are incorporated into the monomer mix. The relative weight % of the functionalized fumaric- and itaconic-containing prepolymers as compared to the total monomer mix weight % is from about 10% to 80%, more preferably from about 10% to 50%, and most preferably 15% to 40%.

Examples of hydrophilic monomers include, but are not limited to, ethylenically unsaturated lactam-containing monomers such as N-vinyl pyrrolidinone; methacrylic and acrylic acids; (meth)acrylic substituted alcohols, such as 2-hydroxyethylmethacrylate (HEMA) and 2-hydroxyethylacrylate; and (meth)acrylamides, such as methacrylamide and N,N-dimethylacrylamide (DMA); vinyl carbonate or vinyl carbamate monomers such as disclosed in U.S. Pat. Nos. 5,070,215; and oxazolinone monomers such as disclosed in U.S. Pat. No. 4,910,277. Other hydrophilic monomers such as glycerol methacrylate and polyethyleneglycol monomethacrylate are also useful in the present invention.

Preferred hydrophilic vinyl-containing monomers that may be incorporated into the hydrogels of the present invention include monomers such as N-vinyl lactams such as N-vinyl pyrrolidinone (NVP), N-vinyl-N-methyl acetamide, N-vinyl-N-ethyl acetamide, N-vinyl-N-ethyl formamide, N-vinyl formamide, with NVP being the most preferred.

Preferred hydrophilic acrylic-containing monomers which may be incorporated into the hydrogel of the present invention include hydrophilic monomers such as N,N-dimethyl acrylamide (DMA), 2-hydroxyethyl methacrylate, glycerol methacrylate, 2-hydroxyethyl methacrylamide, methacrylic acid and acrylic acid, with DMA being the most preferred. Other suitable hydrophilic monomers will be apparent to one skilled in the art. The relative weight % of hydrophilic monomer(s) to total weight % of the comonomer mix is preferably from about 5% to 80%, more preferably from about 20% to 70%, and most preferably 20% to 40%.

As mentioned previously, additional silicone-containing monomers may be present in the monomer mixes with the reactive functionalized fumaric- or itaconic-containing monomers. One preferred class of suitable silicone-containing monomers which may be incorporated into a monomer mix with the reactive functionalized fumaric- or itaconic-containing prepolymers of the present invention are the bulky polysiloxanylalkyl (meth)acrylic monomers represented by the following Formula (I):

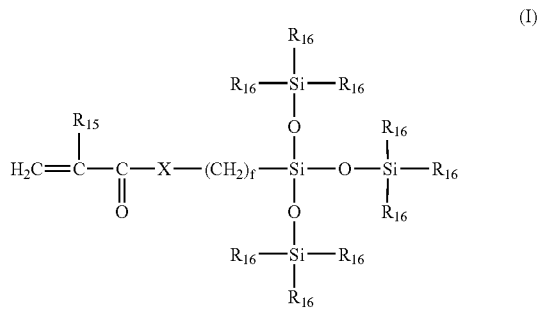

wherein: X is O or NR; each $R_{15}$ is independently hydrogen or an alkyl group having 1 to 10 carbon atoms; and each $R_{16}$ is independently a lower alkyl or phenyl group; and f is 1 or 3 to 10.

Such bulky monomers include methacryloxypropyl tris (trimethylsiloxy)silane (TRIS), pentamethyldisiloxanylmethylmethacrylate, tris(trimethylsiloxy)methacryloxy propylsilane, phenyltetramethyldisiloxanylethyl acrylate, and methyldi(trimethylsiloxy)methacryloxymethyl silane. Further preferred classes of silicone-containing monomers which may be incorporated into a monomer mix with the reactive functionalized fumaric- or itaconic-containing monomers of the present invention are the poly(organosiloxane) monomers represented by the following formula (II):

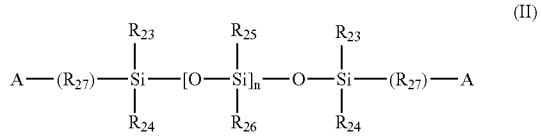

wherein: A is an activated unsaturated group, such as an ester or amide of an acrylic or a methacrylic acid; each $R_{23}$-$R_{26}$ is independently selected from the group consisting of a monovalent hydrocarbon radical or a halogen substituted monovalent hydrocarbon radical having 1 to 18 carbon atoms which may have ether linkages between carbon atoms; $R_{27}$ is a divalent hydrocarbon radical having from 1 to 22 carbon atoms; and n is 0 or an integer greater than or equal to 1. When siloxane-containing monomers other than the functionalized silicone containing prepolymers are incorporated into the monomer mix, the weight % of the other siloxane-containing monomers as compared to the total monomer mix weight % is from about 5% to 60%, more preferably from about 10% to 50%, and most preferably 10% to 40%.

Either the silicone-containing monomer, the functionalized fumaric- or itaconic-containing prepolymer, or the hydrophilic monomer may function as a crosslinking agent (a crosslinker), being defined as a monomer having multiple polymerizable functionalities. Additional crosslinkers also may be present in the monomer mix which polymerizes to form the hydrogel.

Most "known" crosslinking agents are hydrophobic. When it is desirable for both an acrylic-containing monomer and a vinyl-containing monomer to be incorporated into the silicone-containing polymer of the present invention, a further crosslinking agent having both a vinyl and an acrylic polymerizable group may be used, since these vinyl and acrylic monomers have differing reactivity ratios and may not copolymerize efficiently. Such crosslinkers which facilitate the copolymerization of these monomers are the subject of U.S. Pat. No. 5,310,779, the contents of which is incorporated herein by reference. Such crosslinkers are represented by the following schematic representation:

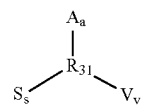

wherein V denotes a vinyl-containing group having the formula:

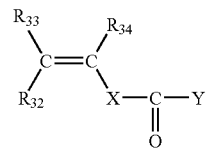

A denotes an acrylic-containing group having the formula:

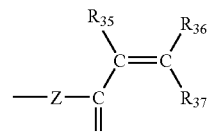

S denotes a styrene-containing group having the formula:

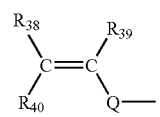

wherein $R_{31}$ is an alkyl radical derived from substituted and unsubstituted hydrocarbons, polyalkylene oxide, poly(perfluoro) alkylene oxide, dialkyl-capped polydimethylsiloxane, dialkyl-capped polydimethylsiloxane modified with fluoroalkyl or fluoroether groups; $R_{32}$-$R_{40}$ are independently H, or alkyl of 1 to 5 carbon atoms; Q is an organic group containing aromatic moieties having 6-30 carbon atoms; X, Y, and Z are independently O, NH or S; v is 1, or higher; and a, s are independently greater than or equal to 0; and a+s is greater than or equal to 1. An example is 2-hydroxyethylmethacrylate vinyl carbonate or carbamate.

Other crosslinking agents which may be incorporated into the silicone-containing hydrogel of the present invention include polyvinyl, typically di- or tri-vinyl monomers, most commonly the di- or tri(meth)acrylates of dihydric ethylene glycol, triethylene glycol, butylene glycol, hexane-1,6-diol, thio-diethylene glycol-diacrylate and methacrylate; neopentyl glycol diacrylate; trimethylolpropane triacrylate and the like; N,N'-dihydroxyethylene-bisacrylamide and-bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentaerythritol, butylene glycol, mannitol, and sorbitol. Further examples include N,N-methylene-bis-(meth)acrylamide, sulfonated divinylbenzene, and divinylsulfone. Also useful are the reaction products of hydroxyalkyl (meth)acrylates with unsaturated isocyanates, for example the reaction product of 2-hydroxyethyl methacrylate with 2-isocyanatoethyl methacrylate (IEM). See U.S. Pat. No. 4,954,587.

Other known crosslinking agents are polyether-bisurethane-dimethacrylates (see U.S. Pat. No. 4,192,827), and those crosslinkers obtained by reaction of polyethylene glycol, polypropylene glycol and polytetramethylene glycol with 2-isocyanatoethyl methacrylate (IEM) or m-isopropenyl-γ, γ-dimethylbenzyl isocyanates (m-TMI), and polysiloxane-bisurethane-dimethacrylates. See U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI.

The prepolymers of the present invention, when copolymerized, are readily cured to cast shapes by methods such as UV polymerization, use of free radical thermal initiators and heat, or combinations thereof. Representative free radical thermal polymerization initiators are organic peroxides, such as for example acetyl peroxide, lauroyl peroxide, decanoyl peroxide, stearoyl peroxide, benzoyl peroxide, tertiary butyl peroxypivalate, peroxydicarbonate, and the commercially available thermal initiators such as LUPERSOL® 256, 225 (Atofina Chemical, Philadelphia, Pa.) and the like, employed in a concentration of about 0.01 to 2 percent by weight of the total monomer mixture. Representative UV initiators are those known in the field such as, benzoin methyl ether, benzoin ethyl ether, DAROCUR®-1173, 1164, 2273, 1116, 2959, 3331, IGRACURE® 651 and 184 (Ciba Specialty Chemicals, Ardsley, N.Y.).

In addition to the above-mentioned polymerization initiators, the copolymer of the present invention may also include other components as will be apparent to one skilled in the art. For example, the monomer mix may include additional colorants, or UV-absorbing agents and toughening agents such as those known in the contact lens art.

The resulting copolymers of this invention can be formed into contact lenses by the spincasting processes such as those disclosed in U.S. Pat. Nos. 3,408,429 and 3,496,254, static casting processes such as in U.S. Pat. No. 5,271,875 and other conventional methods, such as compression molding as disclosed in U.S. Pat. Nos. 4,084,459 and 4,197,266.

Polymerization of the monomer mix may be conducted either in a spinning mold, or a stationary mold corresponding to a desired contact lens shape. The thus-obtained contact lens may be further subjected to a mechanical finishing, as occasion demands. Also, the polymerization may be conducted in an appropriate mold or vessel to give a lens material in the form of button, plate or rod, which may then be processed (e.g., cut or polished via lathe or laser) to give a contact lens having a desired shape.

The hydrogels produced by the present invention are oxygen transporting, hydrolytically stable, biologically inert, and transparent. The monomers and prepolymers employed in accordance with this invention are readily polymerized to form three-dimensional networks which permit the transport of oxygen and are optically clear, strong and hydrophilic.

The present invention provides materials which can be usefully employed for the fabrication of prostheses such as heart valves and intraocular lenses, as optical contact lenses or as films. More particularly, the present invention concerns contact lenses.

The present invention further provides articles of manufacture which can be used for biomedical devices, such as, surgical devices, heart valves, vessel substitutes, intrauterine devices, membranes and other films, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, intraocular devices and especially contact lenses.

It is known that blood, for example, is readily and rapidly damaged when it comes into contact with artificial surfaces. The design of a synthetic surface which is antithrombogenic and nonhemolytic to blood is necessary for prostheses and devices used with blood.

The present invention also provides a method of surface modifying contact lenses and like medical devices through the use of complementary reactive functionality. Although only contact lenses will be referred to hereinafter for purposes of simplicity, such reference is not intended to be limiting since the subject method is suitable for surface modification of other medical devices as well as contact lenses. Reactive hydrophilic polymers are used to form covalent chemical linkages with the surface of contact lenses manufactured from the reactive functionalized fumaric- and itaconic-containing prepolymers of the invention herein. The preferred reactive, hydrophilic polymers for use in the present invention are selected based on the specific reactive functionalized fumaric- and itaconic-containing polymeric material to be coated. In accordance with the present invention, the one or more reactive hydrophilic polymers selected for surface modification must have complementary chemical functionality to that of the reactive functionalized fumaric- and itaconic-containing polymeric materials. Such complementary chemical functionality enables a chemical reaction between the reactive functionalized fumaric- and itaconic-containing polymeric material and the reactive hydrophilic polymer to form covalent chemical linkages therebetween. The one or more reactive hydrophilic polymers are thus chemically bound to the surface of the one or more reactive functionalized fumaric- and itaconic-containing polymeric materials of the contact lens or like medical device to achieve surface modification thereof. For surface modification of contact lenses in accordance with the present invention, complementary reactive functionality is incorporated between the reactive functionalized fumaric- and itaconic-containing prepolymers of the contact lens material and the surface modification treatment polymer (SMTP). For example, if a reactive hydrophilic SMTP has epoxide functionality, then the contact lens material to be treated must have a functionalized fumaric- or itaconic-containing prepolymer having a residue with complementary functionality that will react with that of the SMTP. In such a case, the contact lens material could include a reactive functionalized fumaric-containing prepolymer such as bis-α,ω-fumaryl butyl polydimethyl siloxane, diacid to react with the SMTP epoxide functionality. Likewise, if a contact lens is formed from functionalized fumaric-containing material having a residue providing epoxide reactive, a hydrophilic SMTP containing a 2-hydroxyethyl methacrylate copolymer could be used for surface modification in accordance with the present invention. Examples of complementary functionality are provided below in Table 1.

TABLE 1

| RESIDUE HAVING A REACTIVE FUNCTIONAL GROUP | COMPLEMENTARY FUNCTIONALITY |
|---|---|
| Carboxylic acid, isocyanate, epoxy, anhydride, lactone, lactam, oxazolone | Alcohol, amine, thiol |
| Glycidyl methacrylate (epoxy), anhydride, amine, alcohol | Carboxylic Acid |
| Amine, thiol, alcohol | Oxazolone |
| Carboxylic acid, alcohol, primary amine, thiol | Anhydride |
| Alcohol, carboxylic acid, amine | Epoxide |

More specifically, surface modification of contact lenses having reactive functionalized fumaric- and itaconic-containing copolymers in accordance with the present invention requires one or more reactive, hydrophilic SMTPs. The reactive hydrophilic SMTPs useful in the practice of the present invention are copolymers of various hydrophilic monomers with a monomer having reactive chemical functionality. The hydrophilic monomers can be aprotic types such as acrylamides and N-vinyl pyrrolidinone or protic types such as methacrylic acid and 2-hydroxyethyl methacrylate. Examples of suitable hydrophilic monomers include, but are not limited to, N,N-dimethylacrylamide, N,N-dimethylmethacrylamide, N-methylmethacrylamide and N-methylacrylamide; but preferably N,N-dimethylacrylamide for increased hydrophilicity. Suitable monomers having reactive chemical functionality include for example, but are not limited to, monomers having epoxide, carboxylic acid, anhydride, oxazolone and alcohol functionalities. Examples of suitable reactive, hydrophilic SMTPs include, but are not limited to, copolymers and terpolymers of the monomers having reactive chemical functionality described above. Such reactive, hydrophilic SMTPs are produced through free radical polymerization techniques known to those skilled in the art.

Although the teachings of the present invention are preferably applied to soft or foldable contact lenses or like medical devices formed of a foldable or compressible material, the same may also be applied to harder, less flexible, lenses formed of a relatively rigid material such as poly(methyl methacrylate) (PMMA).

In accordance with the present invention, the reactive functionalized fumaric- and itaconic-containing prepolymers are used to produce a contact lens containing reactive functional groups. One or more reactive, hydrophilic SMTPs as described above, are then selected so as to have chemical functionality complementary to that of the reactive functionalized fumaric- and itaconic-containing prepolymers comprising the contact lens. Such complementary chemical functionality enables a chemical reaction to occur between the functional groups of the reactive functionalized fumaric- and itaconic-containing prepolymer forming the contact lens and the functional groups of the one or more reactive, hydrophilic SMTPs. This chemical reaction between functional groups forms covalent chemical linkages therebetween. For example, a contact lens containing functionalized prepolymer having hydroxyl functional groups would preferably undergo surface modification using reactive, hydrophilic SMTPs containing carboxylic acid functional groups, isocyanate functional groups or epoxy functional groups. Likewise, a contact lens containing functionalized prepolymer having carboxylic acid groups would preferably undergo surface modification using reactive, hydrophilic SMTPs containing glycidyl methacrylate (GMA) monomer units to provide epoxy functional groups. The reaction of the contact lens containing functionalized fumaric- and itaconic-containing reactive functional groups and the reactive hydrophilic SMTPs is conducted under conditions known to those of skill in the art.

The reactive functionalized fumaric- and itaconic-containing prepolymers useful in certain embodiments of the present invention may be prepared according to syntheses well known in the art and according to the methods disclosed in the following examples. Surface modification of contact lenses produced from one or more reactive functionalized fumaric- and itaconic-containing polymeric materials using one or more reactive, hydrophilic SMTPs in accordance with the present invention is described in still greater detail in the examples that follow.

EXAMPLES

Example 1

Preparation of an Acid-Terminated Fumaric Prepolymer [(F2D20-Diacid)]

To a thoroughly dried 500-ml round bottom flask equipped with a reflux condenser was added bis-α, ω-hydroxybutyl polydimethylsiloxane (Mn 1624, 30.08 grams, 0.0185 mole) prepared by following a procedure described in Journal of Polymer Science, Part A. 33, 1773 (1995) and fumaryl chloride (MW 152.96, 6.4013 grams, 0.0418 moles) (Aldrich Chemical, Milwaukee, Wis.). The reaction mixture was heated with an oil bath at 60° C. After two hours, the reaction was complete, as indicated by the loss of $CH_2$—OH peak at 3.5 ppm (in H-NMR). The content of the flask was stripped under vacuum (0.4 mmHg) at 80° C. for 2 hours. To the content was then added 3 mg of water and 30 ml of THF. The mixture was heated under reflux until all acid chloride groups disappeared (by IR 1769 $cm^{-1}$). THF was then stripped from the mixture in a Rotavapor. The residue remaining was then added to 200 mL ether and extracted with 50 mL of water three times. The final residue in ether was dried with magnesium sulfate and then vacuum stripped at 80° C. for two hours. SEC (polystyrene standard): Mn=2001, Mw=3141 (Pd=1.57)

Example 2

Preparation of an Acid-Terminated Itaconate-Polysiloxane Prepolymer (I2D20-Diacid)

To a thoroughly dried 500-mL round bottom flask equipped with a reflux condenser is added bis-α,ω-hydroxybutyl polydimethylsiloxane (Mn 1624, 30.08 grams, 0.0185 mole) and itaconyl chloride (MW 166.99, 6.99 grams, 0.0418 moles). The mixture is heated with an oil bath at 60° C. After two hours, the reaction is complete, as indicated by the loss of $CH_2$—OH peak at 3.5 ppm (in H-NMR). The content of the flask is stripped under vacuum (<0.4 mmHg) at 80° C. for 2 hours. To the content is then added 3 mg of water and 30 mL of THF. The mixture is heated under reflux until all acid chloride groups have disappeared totally (by IR 1769 $cm^{-1}$). THF is then stripped from the product in a Rotavapor. The residue remaining is then added to 200 mL ether and extracted with 50 mL of water three times. The final residue in ether is dried with magnesium sulfate and then vacuum stripped at 80° C. for 2 hours.

Example 3

Preparation of an Acid-Terminated Maleate-Polysiloxane Prepolymer (M2D20-Diacid)

To a thoroughly dried 500-mL round bottom flask equipped with a reflux condenser is added bis-α,ω-hydroxybutyl polydimethylsiloxane (Mn 1624, 30.08 grams, 0.0185 mole), 150 mL of tetrahydrofuran and maleic anhydride (MW 98.06, 4.10 grams, 0.0418 moles). The mixture is heated with an oil bath at 60° C. After sixteen hours, the reaction is complete, as indicated by the loss of $CH_2$—OH peak at 3.5 ppm (in H-NMR). To the content is then added 5 mL of water and continued heating for 2 hours. The solution is dried with magnesium sulfate and then vacuum stripped at 80° C. for 2 hours to give product.

Example 4

Preparation of Hydrogel Films from Fumaric Prepolymer and Other Comonomers

A prepolymer prepared as described in Example 1, 32 parts, was mixed with 32 parts of N,N-dimethylacrylamide, 36 parts of TRIS, 27 parts of hexanol, and 0.3 part Darocur® 1173 initiator (Ciba Specialty Chemical). The mix was cast between two silane-treated glass plates and cured in an oven at 70° C. for an hour. The cured films were then released, extracted in isopropanol, boiled in water for 4 hours and then placed in borate buffered saline. Properties of hydrogel films: Water content 39%, Modulus 36 $g/mm^2$, Tear strength 13 g/mm. Oxygen permeability 93 (Dk unit).

Example 5

Hydrogel Film Preparation—Derived from the Prepolymer Described in Example 1 (Thermal Curing)

A monomer mix was prepared from a prepolymer prepared as described in Example 1, TRIS, DMA and Vazo® 52 initiator (DuPont) at the weight ratio of 20/40/40/1. The mix was then cast and processed into hydrogel films by applying the same procedure as described in Example 4. Properties of hydrogel films: Water content 41%; Modulus 49 $g/mm^2$; Tear strength 3.0 g/mm; Oxygen permeability 63 (DK unit).

Example 6

Lens Casting with Variable Frequency Microwave Curing, Purified with Super Critical Fluid, Followed by Direct Coating A monomer mix consisting of a prepolymer prepared as described in Example 1, a t-butylfumarate end-capped polydimethylsiloxane of Mn 1600, (F2D20), TRIS, DMA and n-hexanol at a ratio of 15/15/30/40/5 was prepared This mix was placed between two polypropylene molds and cured under microwave conditions. After releasing from the molds, the lenses were extracted with $CO_2$ super critical fluid. The lenses were then placed in a distilled water solution containing a hydrophilic polymer derived from glycidyl methacrylate, N, N-dimethyl acrylamide and octafluoropentyl methacrylate (prepared as described in Example 9) and then autoclaved for 30 minutes. The lenses were then transferred to clean vials containing borate buffered saline at pH 7.1 and autoclaved. All lenses before and after treatments with polymer coating were characterized for water content and surface analysis (by XPS). The results were as follows:

TABLE 2

| | % water | % O1S (anterior/posterior) | % N1S (anterior/posterior) | % C1S (anterior/posterior) | % Si1S (anterior/posterior) |
|---|---|---|---|---|---|
| Before Treatment | 43.6 | 19.54/19.30 | 4.03/4.35 | 62.91/63.13 | 13.52/13.22 |
| After Treatment | 46.25 | 18.84/19.24 | 6.3/6.33 | 65.58/65.78 | 8.88/8.02 |

Example 7

Preparation of Hydrogel Films from a Prepolymer and Other Comonomers (UV Curing)

A prepolymer as described in Example 2, 30 parts, is mixed with 30 parts of N,N-dimethylacrylamide (DMA), 40 parts of 3-methacyryloxypropyl tris(trimethylsiloxy)silane (TRIS), 20 parts of Hexanol, and 0.3 part of Darocur-1173. The mix is then cast between two silane-treated glass plates under UV at about 4000 microwatts for two hours. The cured films are then extracted with isopropanol overnight, followed by boiling in water and then placed in borate buffered saline at pH 7.2 to give hydrogel films.

Example 8

Synthesis of Reactive, Hydrophilic Copolymer of N,N-dimethylacrylamide (DMA) and Glycidyl Methacrylate (GMA)

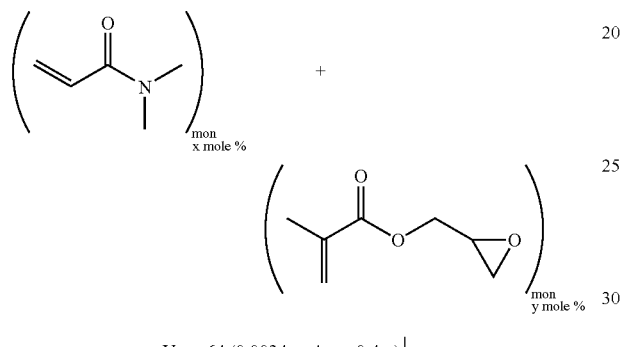

Vazo 64 (0.0024 moles = 0.4 g)
Total Moles of monomer = 2.24

-continued

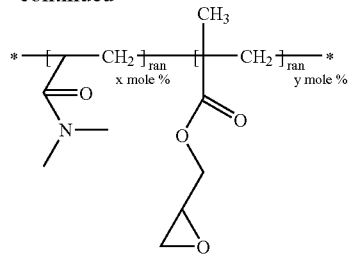

DMA-co-GMA [x=86, y=14] To a 3 liter (L) reaction flask is added distilled N,N-dimethylacrylamide (DMA, 2 g, 1.92 moles), distilled glycidyl methacrylate (GMA, 48 g, 0.32 moles) 2,2'-azobisisobutyronitrile (AIBN, 0.4 g, 0.0024 moles) and tetrahydrofuran (2000 ml). The reaction vessel is fitted with a mechanical stirrer, condenser, thermal controller and a nitrogen inlet. Nitrogen is bubbled through the solution for 15 minutes to remove any dissolved oxygen. The reaction flask is then heated to 60° C. under a passive blanket of nitrogen for 24 hours. The reaction mixture is then added slowly to 12 L of ethyl ether with good mechanical stirring. The reactive polymer precipitates and is collected by vacuum filtration. The solid is placed in a vacuum oven at 30° C. overnight to remove the ether leaving the reactive polymer. The reactive polymer is placed in a desiccator for storage until use.

Example 9

Synthesis of Reactive, Hydrophilic Copolymer of N,N-dimethylacrylamide (DMA), 1H,1H,5H-octafluoropentyl methacrylate (OFPMA) and Glycidyl Methacrylate (GMA)

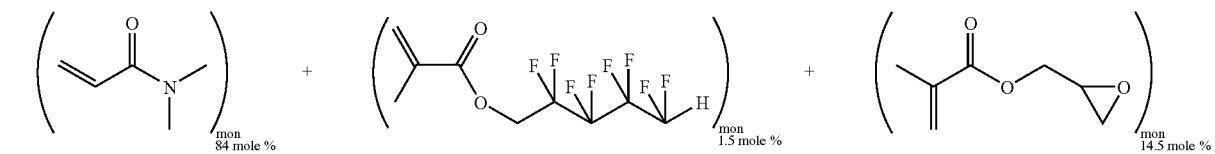

Molecular Weight = 99.13
Molecular Formula = $C_5H_9NO$

Molecular Weight = 300.15
Molecular Formula = $C_9H_8F_8O_2$

Molecular Weight = 142.16
Molecular Formula = $C_7H_{10}O_3$

Vazo 64 (0.00072 moles = 0.12 g)
Total Moles of monomer = 0.764

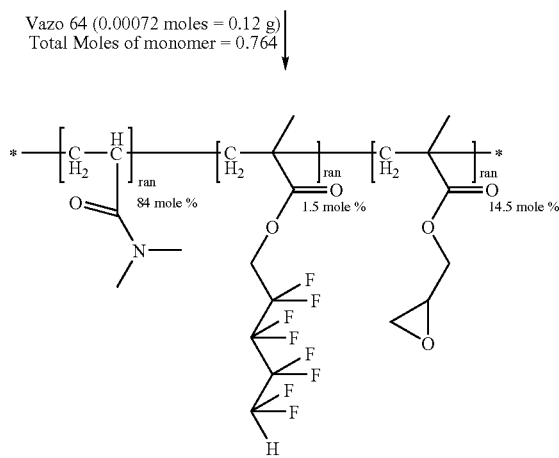

To a 1000 ml reaction flask is added distilled N,N-dimethylacrylamide (DMA, 64 g, 0.64 moles), 1H, 1H, 5H-octafluoropentyl methacrylate (OFPMA, 4 g, 0.012 moles, used as received), distilled glycidyl methacrylate (GM, 16 g, 0.112 moles) 2,2'-azobisisobutyronitrile (AIBN, 0.12 g, 0.00072 moles) and tetrahydrofuran (1200 ml). The reaction vessel is fitted with a magnetic stirrer, condenser, thermal controller and a nitrogen inlet. Nitrogen is bubbled through the solution for 15 minutes to remove any dissolved oxygen. The reaction flask is then heated to 60° C. under a passive blanket of nitrogen for 20 hours. The reaction mixture is then added slowly to 6 L of ethyl ether with good mechanical stirring. The reactive polymer precipitates and is collected by vacuum filtration. The solid is placed in a vacuum oven at 30° C. overnight to remove the ether leaving 66.1 g of reactive polymer (79% yield). The reactive polymer is placed in a desiccator for storage until use.

Example 10

Synthesis of Reactive, Hydrophilic Copolymer of N,N-dimethylacrylamide (DMA), 1H, 1H, 5H-octafluoropentyl Methacrylate (OFPMA), Glycidyl Methacrylate (GMA) and Polyethylene Glycol 1000 Monomethylether Methacrylate (PEGMA)

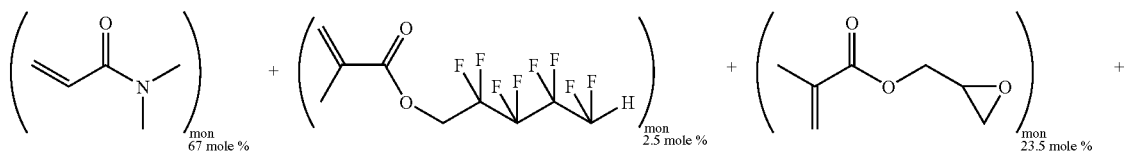

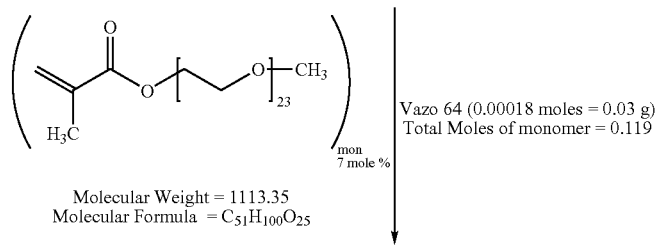

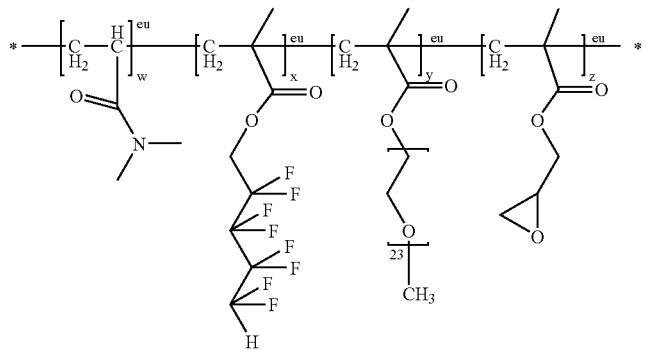

To a 500 ml reaction flask is added distilled N,N-dimethylacrylamide (DMA, 8 g, 0.08 moles), 1H, 1H, 5H-octafluoropentyl methacrylate (OFPMA, 1 g, 0.003 moles, used as received), distilled glycidyl methacrylate (GM, 4 g, 0.028 moles) Polyethylene glycol 1000 monomethylether methacrylate (PEGMA, 8 g, 0.007 moles), 2,2'-azobisisobutyronitrile (AIBN, 0.03 g, 0.00018 moles) and tetrahydrofuran (300 ml). The reaction vessel is fitted with a magnetic stirrer, condenser, thermal controller and a nitrogen inlet. Nitrogen is bubbled through the solution for 15 minutes to remove any dissolved oxygen. The reaction flask is then heated to 60° C. under a passive blanket of nitrogen for 72 hours. Flash evaporation of the solvent followed by freeze drying leaves the reactive polymer, a wax like semi-solid.

Example 11

Synthesis of Reactive, Hydrophilic Copolymer of N-Vinyl-2-pyrrolidinone (NVP) and 4-Vinylcyclohexyl-1,2-epoxide (VCHE)

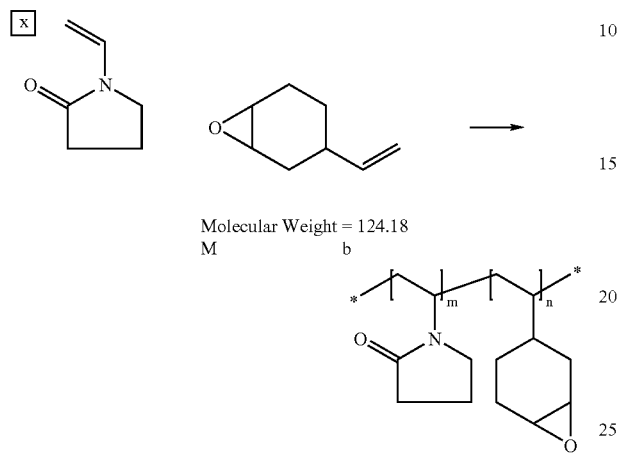

Molecular Weight = 124.18
M            b

To a 1 L reaction flask is added distilled N-vinyl-2-pyrrolidinone (NVP, 53.79 g, 0.48 moles), 4-vinylcyclohexyl-1,2-epoxide (VCHE, 10.43 g, 0.084 moles), 2,2'-azobisisobutyronitrile (AIBN, 0.05 g, 0.0003 moles) and THF (600 ml). The reaction vessel is fitted with a magnetic stirrer, condenser, thermal controller and a nitrogen inlet. Nitrogen is bubbled through the solution for 15 minutes to remove any dissolved oxygen. The reaction flask is then heated to 60° C. under a passive blanket of nitrogen for 20 hours. The reaction mixture is then added slowly to 6 L of ethyl ether with good mechanical stirring. The copolymer precipitates and is collected by vacuum filtration. The solid is placed in a vacuum oven at 30° C. overnight to remove the ether leaving the reactive polymer. The reactive polymer is placed in a desiccator for storage until use.

Example 12

Synthesis of a Reactive Hydrophilic Copolymer of N,N-dimethylacrylamide (DMA), Lauryl methacrylate (LMA) and Glycidyl Methacrylate (GMA)

To a 1000 ml reaction flask is added distilled N,N-dimethylacrylamide (DMA, 32 g, 0.32 moles), lauryl methacrylate (LMA, 1.5 g, 0.006 moles, used as received), distilled glycidyl methacrylate (GM, 8 g, 0.056 moles) 2,2'-azobisisobutyronitrile (AIBN, 0.06 g, 0.00036 moles) and tetrahydrofuran (600 ml). The reaction vessel is fitted with a magnetic stirrer, condenser, thermal controller and a nitrogen inlet. Nitrogen is bubbled through the solution for 15 minutes to remove any dissolved oxygen. The reaction flask is then heated to 60° C. under a passive blanket of nitrogen for 20 hours. The reaction mixture is then added slowly to 3 L of ethyl ether with good mechanical stirring. The reactive polymer precipitates and is collected by vacuum filtration. The solid is placed in a vacuum oven at 30° C. overnight to remove the ether leaving the reactive polymer. The reactive polymer is placed in a desiccator for storage until use.

Example 13

Synthesis of Reactive, Hydrophilic Copolymer of N,N-dimethylacrylamide (DMA) and Methacrylic Acid (MAA)

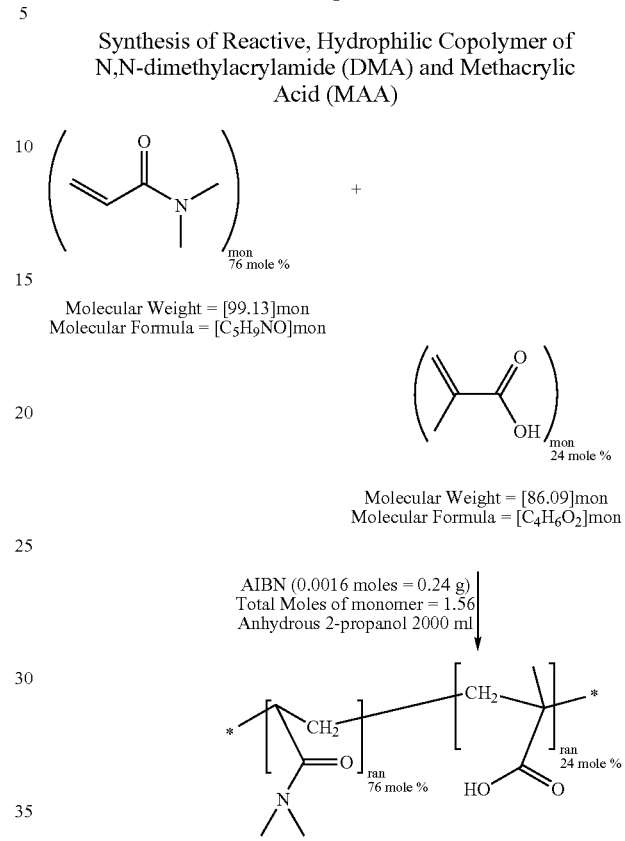

To a 3000 ml reaction flask is added distilled N,N-dimethylacrylamide (DMA, 128 g, 1.28 moles), methacrylic acid (MM, 32 g, 0.37 moles) 2,2'-azobisisobutyronitrile (AIBN, 0.24 g, 0.0016 moles) and anhydrous 2-propanol (2000 ml). The reaction vessel is fitted with a magnetic stirrer, condenser, thermal controller and a nitrogen inlet. Nitrogen is bubbled through the solution for 15 minutes to remove any dissolved oxygen. The reaction flask is then heated to 60° C. under a passive blanket of nitrogen for 72 hours. The volume of the reaction mixture is reduced to half by flash evaporation. The reactive polymer is precipitated into 8 L of ethyl ether and then collected by vacuum filtration. The solid is placed in a vacuum oven at 30° C. overnight to remove the ether leaving the reactive polymer. The reactive polymer is placed in a desiccator for storage until use.

Example 14

Synthesis of a Hydrophilic Reactive Polymer of N,N-dimethylacrylamide (DMA) and 12-Methacryloyloxydodecanoic Acid (LMAA)

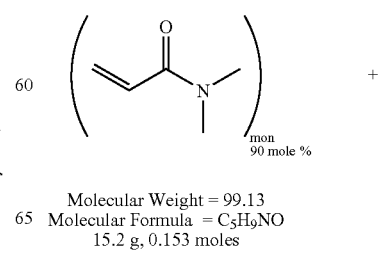

Molecular Weight = 99.13
Molecular Formula = $C_5H_9NO$
15.2 g, 0.153 moles

-continued

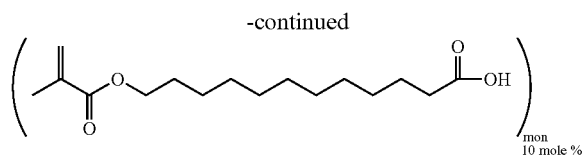

Molecular Weight = 284.4
Molecular Formula = $C_{16}H_{28}O_4$
4.8 g, 0.017 moles Total moles of monomer = 0.17
Vazo 64 (0.0002 moles = 0.032 g) | THF

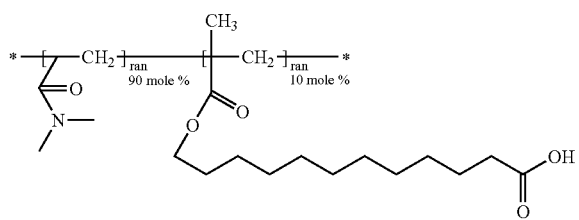

To a 500 ml reaction flask is added distilled N,N-dimethylacrylamide (DMA, 15.2 g, 0.153 moles), 12-methacryloyloxydodecanoic acid (LMAA, 4.8 g, 0.017 moles) 2,2'-azobisisobutyronitrile (AIBN, 0.032 g, 0.0002 moles) and anhydrous tetrahydrofuran (200 ml). The reaction vessel is fitted with a magnetic stirrer, condenser, thermal controller and a nitrogen inlet. Nitrogen is bubbled through the solution for 15 minutes to remove any dissolved oxygen. The reaction flask is then heated to 60° C. under a passive blanket of nitrogen for 72 hours. The reaction mixture is then added slowly to 2.5 L of heptane with good mechanical stirring. The reactive polymer precipitates and is collected by vacuum filtration. The solid is placed in a vacuum oven at 30° C. overnight to remove the ether leaving the reactive polymer. The reactive polymer is placed in a desiccator for storage until use.

Contact lenses manufactured using the unique materials of the present invention are used as customary in the field of ophthalmology. While there is shown and described herein certain specific structures and compositions of the present invention, it will be manifest to those skilled in the art that various modifications may be made without departing from the spirit and scope of the underlying inventive concept and that the same is not limited to particular structures herein shown and described except insofar as indicated by the scope of the appended claims.

What is claimed is:

1. A surface modified medical device comprising:
a medical device manufactured from a monomer mixture containing 20 to 80 weight % of at least one prepolymer selected from the group consisting of reactive functionalized fumaric or itaconic-containing polymeric compounds having the following formula:

and

wherein $R_1$ is selected from the group consisting of alkylenes and alkylenes containing ether linkages, $R_2$ and $R_3$ are independently selected from the group consisting of alkyl groups, phenyl groups, alkyl groups substituted with halogen, phenyl groups substituted with halogen, alkyl groups containing ether linkages and phenyl groups containing ether linkages, W is O or NH, n is an integer between 1 and 10, m is an integer between 2 and 200, and Y is a residue having a reactive functional group selected from the group consisting of hydroxyl, carboxyl, oxazolone, epoxy and anhydride functional groups; and
one or more reactive, hydrophilic polymers applied to the surface of said medical device;
whereby a chemical reaction between said reactive functionalized famaric- or itaconic-containing polymeric material and said one or more reactive, hydrophilic polymers forms covalent bonds therebetween.

2. The surface modified medical device of claim 1 wherein said medical device is a contact lens.

3. The surface modified medical device of claim 2 wherein said one or more reactive, hydrophilic polymers are produced from hydrophilic monomers selected from the group consisting of aprotic and protic hydrophilic monomers.

4. The surface modified medical device of claim 2 wherein said one or more reactive, hydrophilic polymers are produced from hydrophilic monomers selected from the group consisting of N,N-dimethylacrylamide, N,N-dimethylmethacrylamide, N-methylmethacrylamide and N-methylacrylamide.

5. The surface modified medical device of claim 2 wherein said one or more reactive, hydrophilic polymers are produced from hydrophilic monomers having reactive chemical functionality selected from the group consisting of epoxide functionality, carboxylic acid functionality, anhydride functionality, oxazolinone, lactam, lactone functionality and alcohol functionality.

6. The surface modified medical device of claim 2 wherein said one or more reactive, hydrophilic polymers is polydimethylacrylamide-co-glycidylmethylacrylamide).

* * * * *